(12) United States Patent
Jose et al.

(10) Patent No.: US 10,054,602 B2
(45) Date of Patent: Aug. 21, 2018

(54) CONJUGATE OF ESTRADIOL AND APPLICATIONS THEREOF

(71) Applicant: CHRIST UNIVERSITY, Bengaluru, Karnataka (IN)

(72) Inventors: Iven Jose, Bangalore (IN); Shubhada V. Chiplunkar, Navi Mumbai (IN); Vinay Jha Pillai, Bengaluru (IN); Rahul Verma, Gurgaon (IN)

(73) Assignee: CHRIST UNIVERSITY, Bengaluru (IN)

( * ) Notice: Subject to any disclaimer, the term of this patent is extended or adjusted under 35 U.S.C. 154(b) by 13 days.

(21) Appl. No.: 15/682,047

(22) Filed: Aug. 21, 2017

(65) Prior Publication Data
US 2018/0052180 A1    Feb. 22, 2018

(30) Foreign Application Priority Data

Aug. 19, 2016 (IN) .............................. 201641013646

(51) Int. Cl.
| | |
|---|---|
| *A01N 37/00* | (2006.01) |
| *A61K 31/21* | (2006.01) |
| *G01N 33/74* | (2006.01) |
| *C09B 23/08* | (2006.01) |
| *C07J 43/00* | (2006.01) |
| *C07H 1/00* | (2006.01) |
| *C09K 11/06* | (2006.01) |
| *C07H 5/06* | (2006.01) |

(52) U.S. Cl.
CPC ............. *G01N 33/743* (2013.01); *C07H 1/00* (2013.01); *C07H 5/06* (2013.01); *C07J 43/003* (2013.01); *C09B 23/086* (2013.01); *C09K 11/06* (2013.01); *C09K 2211/1018* (2013.01); *G01N 2333/723* (2013.01)

(58) Field of Classification Search
None
See application file for complete search history.

(56) References Cited

U.S. PATENT DOCUMENTS

| | | | |
|---|---|---|---|
| 5,588,032 | A | 12/1996 | Johnson et al. |
| 5,677,125 | A | 10/1997 | Holt et al. |
| 6,543,933 | B2 | 4/2003 | Stergiopoulos et al. |
| 2007/0292352 | A1 | 12/2007 | Marnett et al. |

OTHER PUBLICATIONS

Jose et al, J Fluoresc (2011) 21:1171-1177 (Year: 2011).*
Edrich, J. "Centimeter- and Millimeter-Wave Thermography—A Survey on Tumor Detection". Journal of Microwave Power, vol. 14:2, pp. 95-104, DOI:10.1080/16070658.1979.11689135, 1979.

* cited by examiner

*Primary Examiner* — Jean P Cornet
(74) *Attorney, Agent, or Firm* — Oliff PLC

(57) ABSTRACT

The present invention relates to conjugate of 17-β estradiol with an analog of indocyanine green dye for the detection of cancers. The invention also provides a method of preparation of the conjugate and method of detection of cancer cells.

6 Claims, 7 Drawing Sheets

(A)  (B)

(A)  (B)

CONJUGATE OF ESTRADIOL AND APPLICATIONS THEREOF

FIELD OF INVENTION

The present invention relates to the field of biomedical imaging. The invention provides a conjugate of estradiol with cyanine dyes. In particular, to the conjugate of 17-β estradiol with an analogue of indocyanine green dye for the detection of cancer cells and composition thereof. The invention also provides a method of preparation of the conjugate and method of detection of cancer.

BACKGROUND OF INVENTION

Breast cancer is one of the most common forms of cancer in women. The mortality reported due to breast cancer is increasing at a frightening rate across the globe. Progression of cancer starts from pre-malignant to malignant to metastatic disease which causes death of the patient. There are various modalities used in the detection of these cancers they are X-ray, CT scans, MRI scans, PET, Ultra sound and the like. But, these imaging modalities are difficult to interpret breast cancer lesion, as it gets shadowed by the denser tissues, especially when the breast density is high. Unfortunately, by the time cancer metastasis becomes clinically evident with today's imaging techniques, the metastatic disease gets progressed to late stage prohibiting early successful interventions such as surgery or radiations.

Most of the cancers in women are hormone dependent, the cancerous cells grow by feeding on the hormone, Estrogen. Estrogen stimulates breast cancer cell growth, in the same manner it is responsible for cell growth and division in breast cells. As Estrogen remains a central factor in stimulating breast cancer cell growth, designing new therapeutic strategies to block estrogen stimulation of breast cancer cell growth is important to control the cancer cell growth.

Mammography or other X-Ray methods are currently in widespread use for the detection of breast cancers. The ionizing radiation properties of the X-rays used during the mammogram comes with a risk of having a breast tumor. Additionally, 5-25 percent of malignant breast cancer goes undetected with mammogram and this method is not capable of determining whether the tumor is benign or malignant.

U.S. Pat. No. 6,543,933 discloses a microwave thermography apparatus but it doesn't achieve adequate depth of penetration and the required resolution, except for large cancers. Thus, the small cancer lesions will be undetected.

U.S. Pat. No. 5,588,032 discloses an Apparatus and method for imaging with wave fields using inverse scattering techniques to detect cancer by computational matrix method but the results are vague and cannot be completely relied on for treatment of the patients.

Centimeter- and Millimeter-Wave Thermography—A Survey on Tumour Detection, J. Edrich, p 95-104, states a method, where, the radiometry involved remote sensing by focussed apertures like lenses or reflectors that focus the cm or mm wave into a horn antenna mounted on a scanner, but wavelength of higher frequencies are preferred which have decreased penetration, thus it cannot give clear results due to thick density of tissue.

U.S. Pat. No. 5,677,125 discloses a method for detecting differential expression of marker gene in DCIS (ductal carcinoma situ) pre-invasive cancerous breast tissue. This method could have been desirable but there no detailed study on the function of novel sequences identified. The melanoma and breast cancer markers cannot detect breast cancer with high specificity and sensitively. This is because tumor cells exhibit wide phenotypic diversity during disease progression.

US20070292352 discloses the use of cyanine dyes, but cyanine are not stable in the presence of ammonium hydroxide, dithiothreitol (DTT), primary and secondary amines, and ammonium persulfate (APS) which is commonly used in bioassays. Also, the free dyes used have a poor tumor selectivity.

Considering the importance of detection of cancer cells and challenges associated with current methodologies, it is imperative to develop compounds and techniques which can be adopted in a facile manner and detect cancer cells cost effectively. Since early detection is the key to arrest breast cancer cell growth. The present invention is also related to effective and early detection of breast cancer cells.

Statement of Invention

Accordingly the present invention provides a conjugate of formula A

Formula A

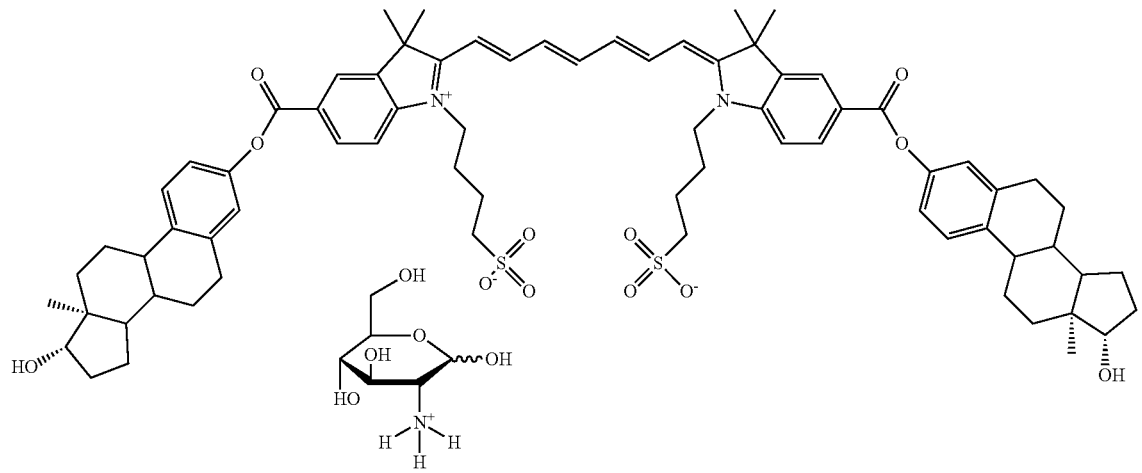

A method of preparation of conjugate of formula A,

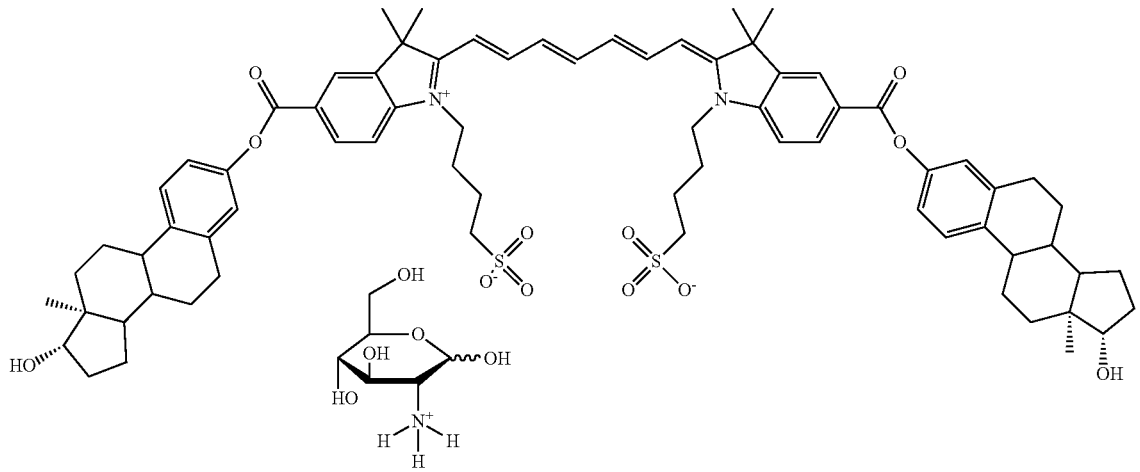

said method comprising acts of a) preparing of compound of formula 3; and

Formula 3

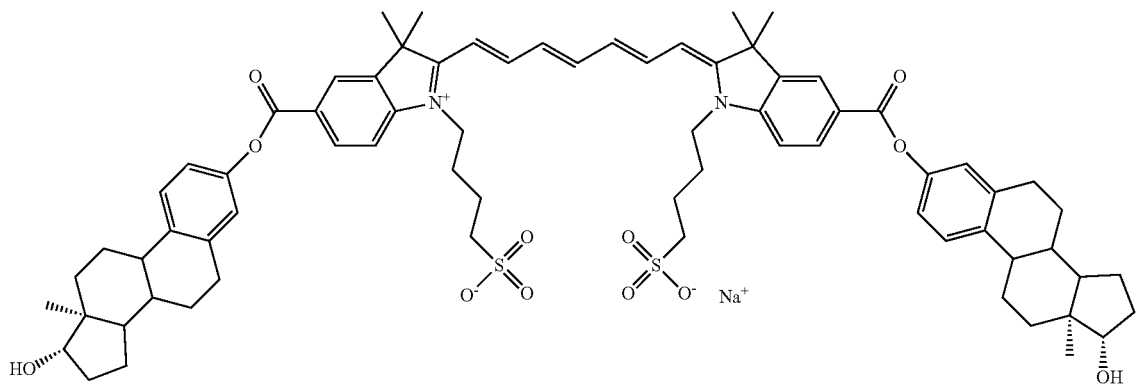

3 treating compound of formula 3 with D-glucosamine hydrochloride to obtain compound of formula A; and a method of detection of cancer cells, said method comprising act of a) staining the cells with conjugate of formula A; and b) comparing the fluorescence intensity generated by the conjugate of formula A at nucleus and the entire cell to detect cancer cells.

BRIEF DESCRIPTION OF DRAWINGS

The features of the present invention can be understood in detail with the aid of appended figures. It is to be noted however, that the appended figures illustrate only typical embodiments of this invention and are therefore not to be considered limiting of its scope for the invention.

FIG. 5.

DETAILED DESCRIPTION OF INVENTION

Figure 1:
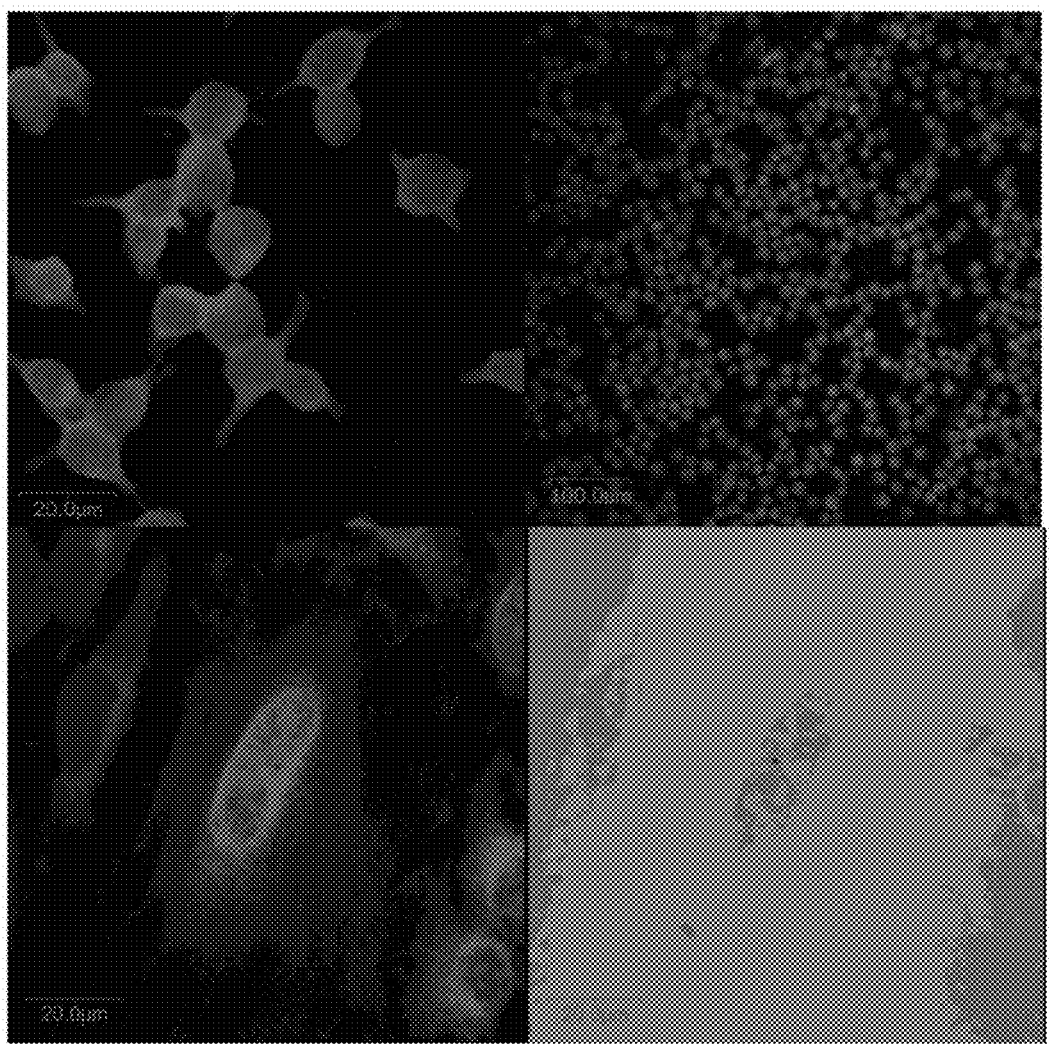
FIG. 1: shows confocal laser scanning microscopy images of MCF-7 and "Differential Interference Contrast (DIC)", transfected MCF-7 cells expressing the estrogen receptor positive which have efficiently bound and internalized the ligand, demonstrating the high specificity of the conjugate.

The foregoing description of the embodiments of the invention has been presented for the purpose of illustration. It is not intended to be exhaustive or to limit the invention to the precise form disclosed as many modifications and variations are possible in light of this disclosure for a person skilled in the art in view of the Figures, description and claims. It may further be noted that as used herein and in the appended claims, the singular "a" "an" and "the" include plural reference unless the context clearly dictates otherwise. Unless defined otherwise, all technical and scientific terms used herein have the same meanings as commonly understood by person skilled in the art.

The present invention is in relation to a conjugate of formula A

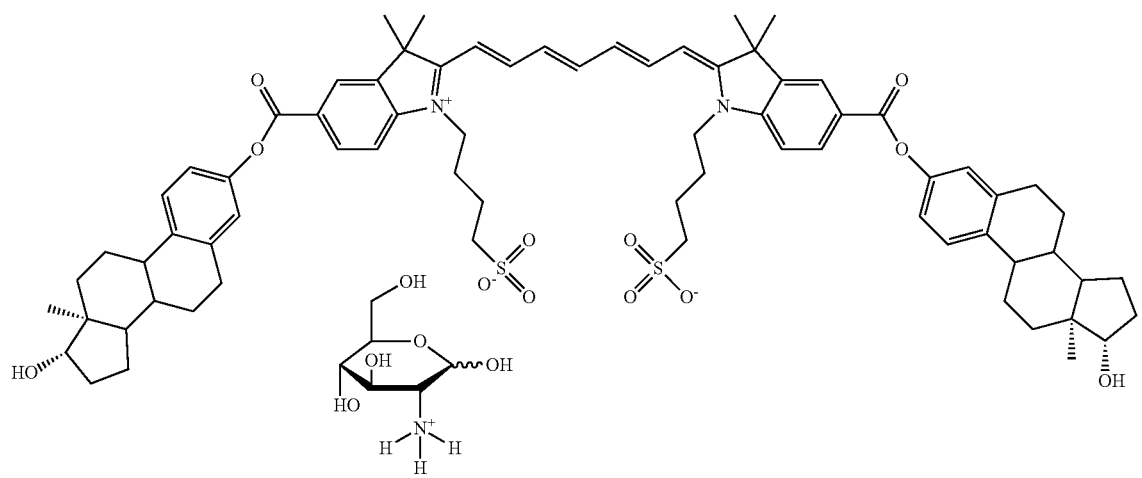

Formula A

The present invention is also in relation to a method of preparation of conjugate of formula A,

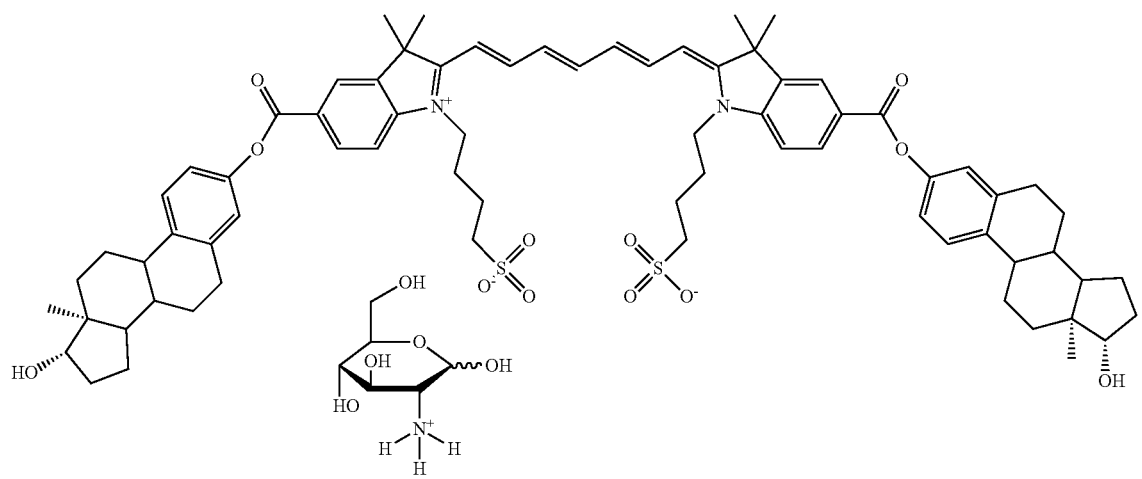

said method comprising acts of
a) preparing of compound of formula 3; and

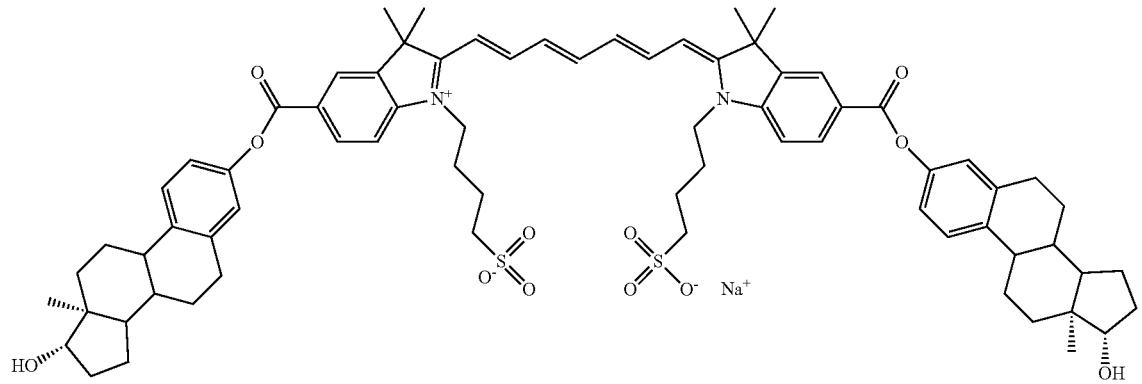

Formula 3 b) treating compound of formula 3 with D-glucosamine hydrochloride to obtain compound of formula A.

In an embodiment of the present invention, the compound of formula 3 is treated with D-glucosamine hydrochloride in presence of trimethylamine.

In another embodiment of the present invention, the compound of formula 3 is treated with D-glucosamine hydrochloride at a temperature ranging from 0° C. to 3° C.

The present invention is also in relation to a method of detection of cancer cells, said method comprising act of
a) staining the cells with conjugate of formula A; and
b) comparing the fluorescence intensity generated by the conjugate of formula A at nucleus and the entire cell to detect cancer cells.

In still another embodiment of the present invention, the comparison shows increased fluorescence at the nucleus of the stained cells.

The present invention provides a near infra-red fluorescent dye, a conjugate of estradiol with a cyanine dye to detect the estrogen receptors and thereby deciding the treatment regime of the patient. The near infrared imaging is used to image the deeper tissues as the dye enhances the specificity and sensitivity of the disease detection apart from enhancing the imaging effect. The absorption and scattering properties of the near Infra Red (NIR) light also helps in differentiating between the normal and diseased tissue volume. This technique helps in non-invasive detection of estrogen receptor status in-vivo and thereby reduces the trauma the patient undergoes during the common invasive procedures for detection of cancer.

An embodiment of invention provide for a conjugate of estradiol and cyanine dye. The invention also provides for a method for preparation of the conjugate. The said conjugate can be used either solely or in combination with other pharmaceutically acceptable compounds.

In particular the present invention is directed to a conjugate (Formula A) of 17-β estradiol with a cyanine dye for use in the early diagnosis of cancers.

Formula A

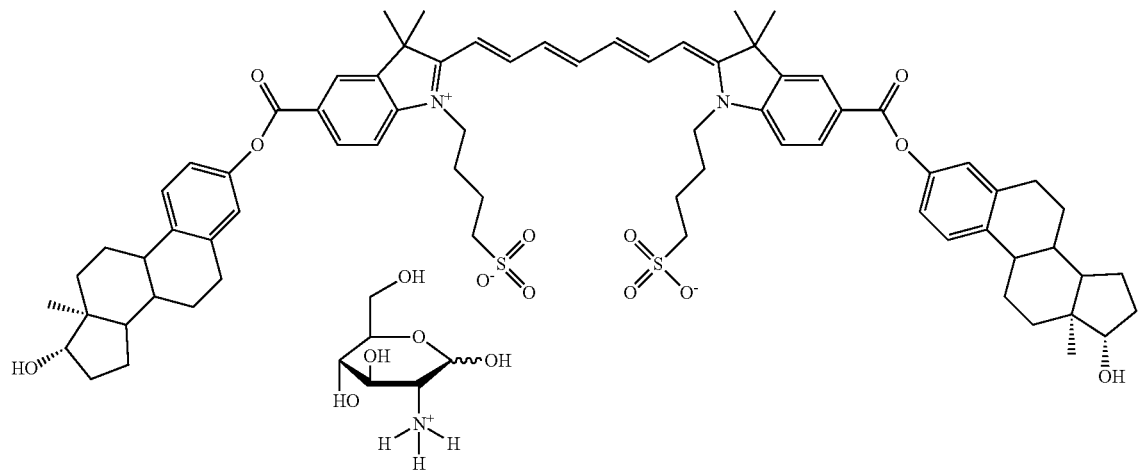

The dye is a derivative of indocyanine green (ICG) i.e., bis 1,1-(4-sulfobutyl)indotricarbocyanine-5-carboxylic acid sodium salt. The replacement of sodium ion in the ester by a larger glucosammonium ion is found to enhance the hydrophilicity, less plasma protein binding (<50%), and thus have different pharmacokinetic properties compared with ICG and exhibits reduce the toxic effect on the cell lines.

The conjugate enhances fluorescence quantum yields by 7-15% in a physiological environment with respect to ICG. In comparison with ICG, the conjugate also exhibit a considerably enhanced tissue-efflux half-life (73 min versus less than 10 min for ICG in tumor tissue), a two-fold higher initial tissue absorption coefficient compared to ICG, and also generated an elevated tumor-to-tissue concentration gradient for up to one hour after injecting.

Furthermore the capability of the conjugate to emit red shifted fluorescent light introduces an independently detectable, spectrally separated signal, thus providing an alternative detection opportunity. The compound can act as suitable NIR contrast agent by enhancing absorption contrast and by providing a dye-specific fluorescence contrast above low auto-fluorescence background. The conjugate formed is found to have an extra binding ability with the receptor cites as compared to ICG, which is established by the partition coefficient studies. This cyanine dye has a partition coefficient less than 0.005 as compared to that of ICG (>200).

The NIRDC conjugate exhibited a 38 nm Stokes' shift of fluorescence maximum. The Quantum yield of the ester is calculated both in DMSO and PBS and is found to be 0.114 and 0.110 respectively, and does not differ significantly between PBS and DMSO. The absorption maxima of the conjugate is shifted to a shorter wavelength of 757 as compared to ICG at 780 which could be attributed due to the omission of the fused benzene rings of ICG. The increased fluorescence quantum yield of the hydrophilic derivatives reduces the risk of the forming fluorescence-quenched aggregation. The table 1 provides the comparative analysis with ICG as standard ($\varphi$=0.13). Thus the conjugate can be used for tagging estradiol because of its ability to form monoderivatized activated precursors as it has a carboxylic group which can be tailored to attach to functional groups of biomoloecules like estradiol.

TABLE 1

Optical Properties of dye

| Conjugate Compound | Solvent | $\lambda_{max}$ absorption (nm) | $\lambda_{max}$ emission (nm) | Stokes' shift | Quantum yield $\varphi$* |
|---|---|---|---|---|---|
| NIRD Con. | DMSO | 757 | 787 | 30 | 0.114 |
| NIRD Con. | PBS | 755 | 788 | 33 | 0.110 |

The excitation and emission peaks for the conjugate are recorded in the NIR region as 757 nm and 788 nm respectively. The potential of the compound in the application as contrast agents for fluorescence imaging modalities, where the fluorescence emission of the dye is expected to be detectable in high sensitivity above low tissue background is analysed on the breast cancer cell lines MCF-7/MDA-MB-231.

The tagging characteristics are pivotal determinants underlying the ability of the fluorescent conjugate in binding the estrogen receptor of the breast cancer cells. The conjugate is tested on the Non-invasive Ductal Carcinoma, Non-invasive Lobular Carcinoma and Non-invasive Adenocarcinoma and Medullary Carcinoma. Each of these tissue yielded ER staining which are confined to the nuclei. The estradiol against ER used in the study clearly indicated the binding on to the cytoplasmic as well as to the nuclear form of ER.

Specific binding and endocytosis of the Estrogen-labeled conjugate is studied on the adenocarcinoma breast cancer cells MCF-7 (estrogen receptor positive) and MDA-MB-231 (estrogen receptor negative). On staining these cell lines with the conjugate, the MCF-7 cells showed almost 2.4-fold higher signal intensity compared to MDA-MB-231 (24 h). The MCF-7 cells showed specific high affinity binding sites of estrogen molecule on to the nucleus and membrane of the estrogen receptor positive cells, whereas the control, MDA-MB-231 showed only the plasma membrane staining. The dye is able to detect lesion size as small as less than 2 mm through molecular imaging.

The study is validated by treating the above mentioned cells with Tamoxifen and Diethylstilbestrol which inhibited the entry of the estradiol into the nucleus of the MCF-7 cells. Further on the staining for ER in the cold formalin fixed paraffin sections showed promising results. The ER-specific binding covered the nucleus of the positive cells diffusely, the distribution of positive nuclear staining varied considerably, depending on the area within a section. Although no cytoplasmic staining is observed in the frozen sections, it is seen in a few paraffin sections. The percentage of ER-positive cells ranged from 5% to 72% in paraffin sections. The nuclear staining specific for ER is positive in most of the tumors in the paraffin sections.

Experimental:

A. Materials and Methods

Cell Lines and Reagents.

Human breast cancer cell lines MCF-7 [ER+] and MDA-MB-231 [ER-] are obtained from National Centre for Cell science (NCCS (Pune)). The cells are cultured, revived and the experiments are carried out at Advanced Centre for Treatment, Research and Education in Cancer (ACTREC) of Tata Memorial Centre (Mumbai).

Cultures and NIRF Assay.

MCF-7 and MDA-MB-231 cells are cultured in DMEM/F12 medium without phenol red (ACTREC, Mumbai) supplemented with 10% fetal bovine serum. Cells in suspension (50 µl) are added to each well of a 96-well culture plate for a final concentration of 1×10$^3$ Cells/well and incubated for 24 h at 37° C. in carbon dioxide chamber.

The NIRFDC with initial concentration of 24.5 mg/2 ml of DMSO solution is added to each well, and the cultures further incubated for 2 h. The cells are treated at different concentration levels of 1:10, 1:50, 1:100, 1:500 and 1:1000 of DMSO. The cells were then re-suspended in 100 µl of 0.04N HCl/isopropanol solution.

B. Staining Protocol for ER Binding, Preparation of Direct Cell Smears Using Cytospin.

Method 1:

Cell smears are prepared by rolling the swab across the top half of the well of a microscope slide. The opposite side of the swab is rolled over the bottom half of the well. There after the slide is allowed to air dry completely. Then the slide is fixed in chilled (2° to 8° C.) acetone for 10 minutes, which is further removed and allowed to air dry completely. Slides are stored at ≤−20° C. with desiccant. On completion, the cells are re-suspend to at least 400 µL in phosphate buffered saline and 200 µL is applied to each slide by cento-centrifugation at 800 rpm for 4 minutes [*Br. J Cancer.* 58:77-80, (1988)]. This procedure is repeated for fixing both the cell lines.

Intracellular Staining.

The smears are stained with the conjugate at different dilutions of 1:10, 1:50, 1:100, 1:500 and 1:1000 and incubated for an hour at about 25° C. Thereafter these cells are given 3 washes of phosphate buffered saline, mounted with DPX (Distrene Plasticyser Xylene) covered and imaged using the Olympus Confocal microscope.

Method 2:

MCF-7 cells maintained at 37° C. in a 5% $CO_2$ atmosphere in phenol red-free minimal essential medium (MEM) containing 10% charcoal stripped calf serum and penicillin, streptomycin, glutamine, are incubated for 4 days in 24 multiwells (NUNC). After 4 days of culture, the medium is removed and the cells are incubated for 1 hour at 37° C. with 1 µM of NIRFDC at concentrations ranging from 0.3 nM to 1 nM. Medium is removed and the cells are washed twice with phosphate buffer saline (PBS). 250 µl of absolute ethanol is added to each well (exposition during 20 min).

C. Tissue Staining Procedure.

Estrogen receptor (ER) in human breast cancer tissues is demonstrated in paraffin sections. The avidin-biotin-peroxidase complex method is used for the paraffin sections fixed in cold buffered formalin and the results are compared with the ER content in the respective tumor tissue. The specific staining for ER is located exclusively in the nuclei of cancer cells in paraffin sections. Differences in the intensity and distribution of nuclear staining within a section were often observed, suggesting heterogeneity of the ER content of individual breast cancer cells.

D. Tissue Preparation and ER Staining for Paraffin Sections.

The tumor pieces are fixed in buffered formalin (0.1 M sodium phosphate, pH 7.4/10% formalin) for 24 hr at 40° C. After being rinsed overnight at 40° C. in 0.1 M sodium phosphate (pH 7.4), they are dehydrated with graded ethanol and embedded in paraffin. Paraffin sections (4 µm) are cut, deparaffinized with xylene, and rinsed thoroughly with absolute ethanol. Then they are soaked in absolute methanol containing 0.3% $H_2O_2$ for 30 min at 25° C. to decrease the endogenous peroxidase activity. The sections were washed three times with 50 mM Tris-HCl, pH 7.6/137 mM NaCl (Tris/NaCl) and were incubated with serum (10% in Tris/NaCl) for 30 min at 25° C. so as to reduce the nonspecific staining. Excess serum is removed by blotting. I~g/ml) or with normal rat IgG (10 A·g/ml) for 30 min at 37° C. After being washed with Tris/NaCl. This is followed by another washing with Tris/NaCl and a subsequent reaction with 3,3'-diaminobenzidine tetrahydrochloride (DAB) solution (0.05 M ammonium acetate/citric acid, pH 5.5-6.0) containing 0.0075% H2O2 and 0.2 mg of DAB per ml) for color development (28) in the dark for 6 min.

E. Testing on MCF-7 Cell Lines

A. Fluorescence Measurement

The in-vitro studies are carried out using the inverted lens Olympus Fluo-View Confocal Microscope. The sample is excited at 754 nm and the emissions are observed using PMT having relatively higher quantum efficiency in the NIR-region.

B. Specificity of 17-β-Estradiol Binding, Confocal Laser Microscopy

To demonstrate that the dye conjugate can act as specific binding ligands for estrogen receptors, it is tested on mammary epithelial cells MCF-7. These cells retained several characteristics of differentiated mammary epithelium including ability to process estradiol via Nuclear and cytoplasmic estrogen receptors and the capability of forming domes. MBA-MB-231 breast cancer cell lines are used as the control. The cells are incubated for 1 h in the presence of 1 µM NIRFDC at 4° C. under conditions allowing internalization The FIG. 1) displays the Confocal laser scanning microscopy images of MCF-7/MDA-MB-231 cells showing the specific binding and endocytosis of the Estrogen-labeled conjugate. Specifically FIG. 1) shows the Confocal images taken at varied resolutions of 100 micro meter, 50 micro meter 20 micro meter and 10 micro meter. These images show very clear localization of conjugated dye in the nucleus of MCF-7 (ER+) cell lines. The cell proliferation is controlled by estrogen. The functional group associated with the dye is instrumental in perculating the dye into the nucleus of MCF-7 cell lines and providing a very unique distinction between the cells and background. The nuclear staining is pivotal towards early detection of cancer as 80% of the breast cancer reported are ER+ and could be detected by this characteristic feature. This feature would also result into avoiding unnecessary biopsies. The specificity of the dye is observed when administered to ER+ Cell lines. This feature actually makes the conjugate highly specific than ICG. ICG on the other end only stains the cells without entering the nucleus of the cell. The DIC image actually shows the existence of the cell in the region of interest and also shows the differential interference contrast image.

Thus when the cancerous cells are incubated in the presence of NIRFD-conjugate in the cold, the majority of the receptor-associated fluorescence co-localized at the Nucleus and a minority in the plasma membrane of transfected receptor expressing cells of MCF-7. After additional incubation under conditions permitting membrane traffic and thus endocytosis, fast and thorough internalization of ligand-receptor complexes into an intracellular compartment could be detected. Again, fluorescence signal of the conjugate largely co-localized and specific high affinity binding sites of 17-beta estradiol is observed as shown in figures.

F. Testing on MDA-MB-231 Cells

Figure 2:
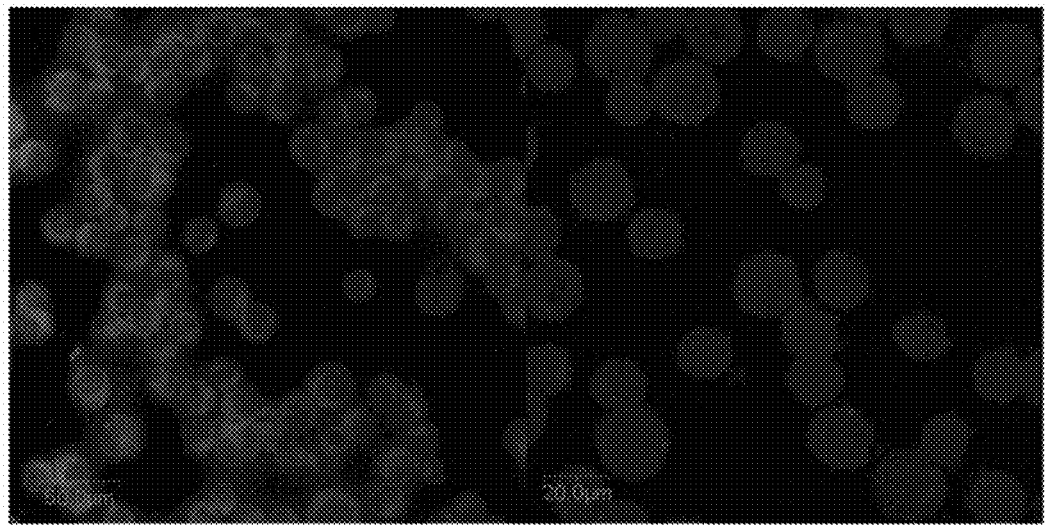
FIG. 2: shows confocal laser scanning microscopy images of MDA-MB-231 and "Differential Interference Contrast (DIC)", transfected MCF-7 cells expressing the estrogen receptor negative cells which have efficiently bound at the cytoplasmic region, demonstrating the absence of entry into the nucleus.

The FIG. 2 shows the Confocal images of MDA-MB-231 (control) ER-ive cells taken at varied resolustions of 50 micro meter and 20 micro meter. The cell lines are not controlled by the estrogen and lack the estrogen activity in the nucleus. After additional incubation under conditions permitting membrane traffic and thus endocytosis, fast and thorough internalization of ligand-receptor complexes into an intracellular compartment could be detected. Again, fluorescence signal of these molecules largely co-localized and specific High affinity binding sites of 17-beta estradiol is observed as shown in the FIG. 2. Hence the co-localization of the dye only in the cytoplasmic areas and a void in the nuclear region is observed. This feature would also result into avoiding unnecessary biopsies. Thus the staining of ER-ive cells would get confined to the cytoplasmic areas only.

G. DES (Diethylstilbestrol) Treatment

Inhibition of the Estrogenic Activity by DES Treatment.

Figure 3:
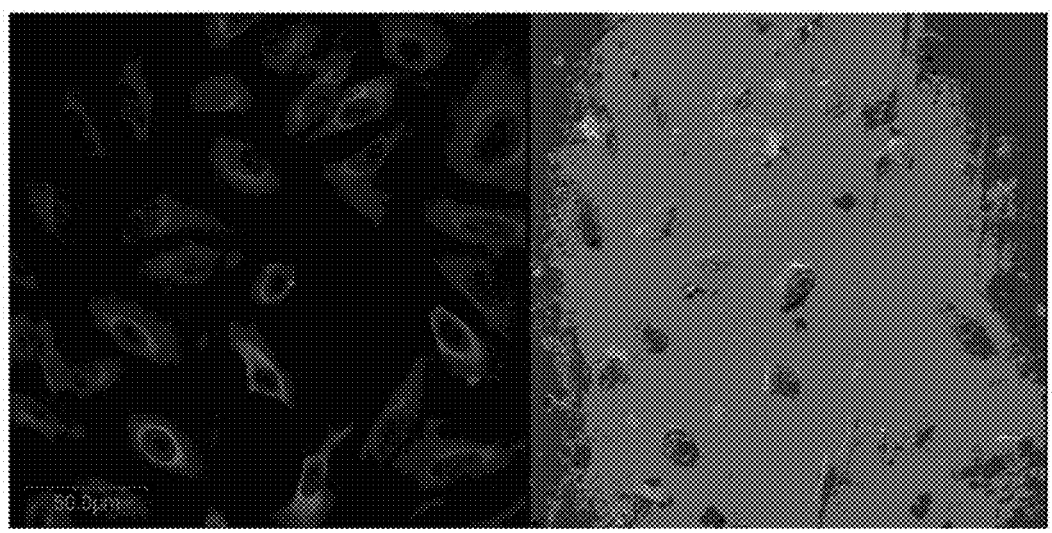
FIG. 3: shows estrogenic activity using DES; DES treated image and their DIC image

The estrogenic activity is examined using human mammary carcinoma MCF-7 cells. The cells are cultured with various concentrations of Diethylstilbestrol (DES) and estrogen conjugated dye for more than 5 days and then the cells were counted. The FIG. 3 clearly demonstrates the blocking operation of the estrogen conjugated dye from entering the nucleus.

H. Effect of Tamoxifen and ICG.

Figure 4:
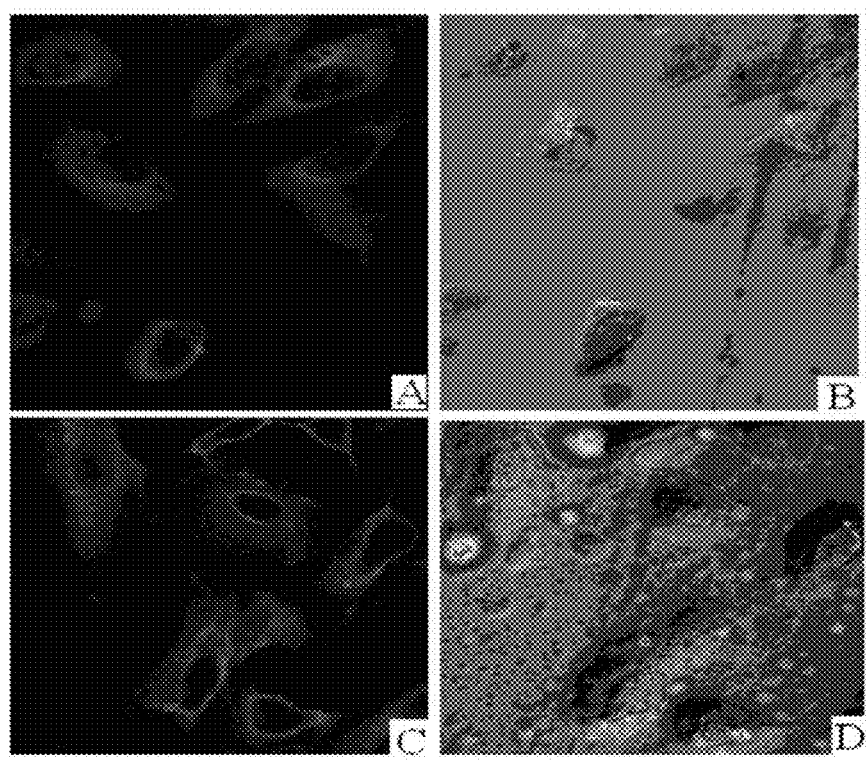
FIG. 4: shows estrogenic activity using Tamoxifen and ICG; A-tamoxifen treated C-ICG treated, B,D-respective DIC images.

Tamoxifen is the drug generally given to block the estrogenic activity in a breast cancer and ICG is the commercially available fluorescent dye used for staining the cells. The MCF-7 cells are treated separately with tamoxifen and commercially available dye Indocyanine Green (ICG). The cells in the FIG. 4 shows the blocking operation of the estrogen conjugated dye entering the nucleus of the cell. A very clear distinction on non-specific binding is observed and the binding is only seen in the cytoplasm.

I. ER Immunoperoxidase Staining.

Figure 5A:
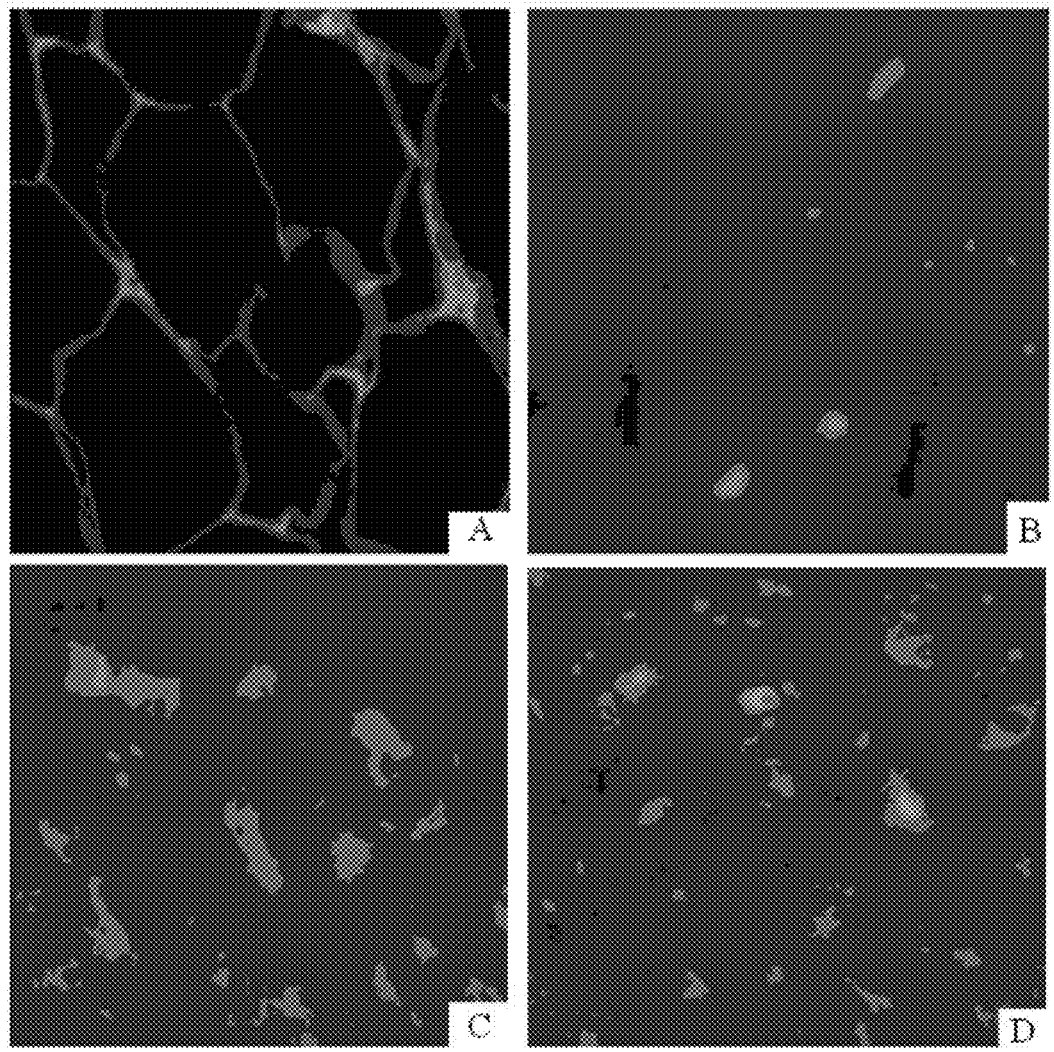
FIG. 5A provides ER binding of Non-invasive Ductal Carcinoma; A. The control; B,C,D. Specific Nuclear binding of the Estrogen receptors.
Figure 5B:
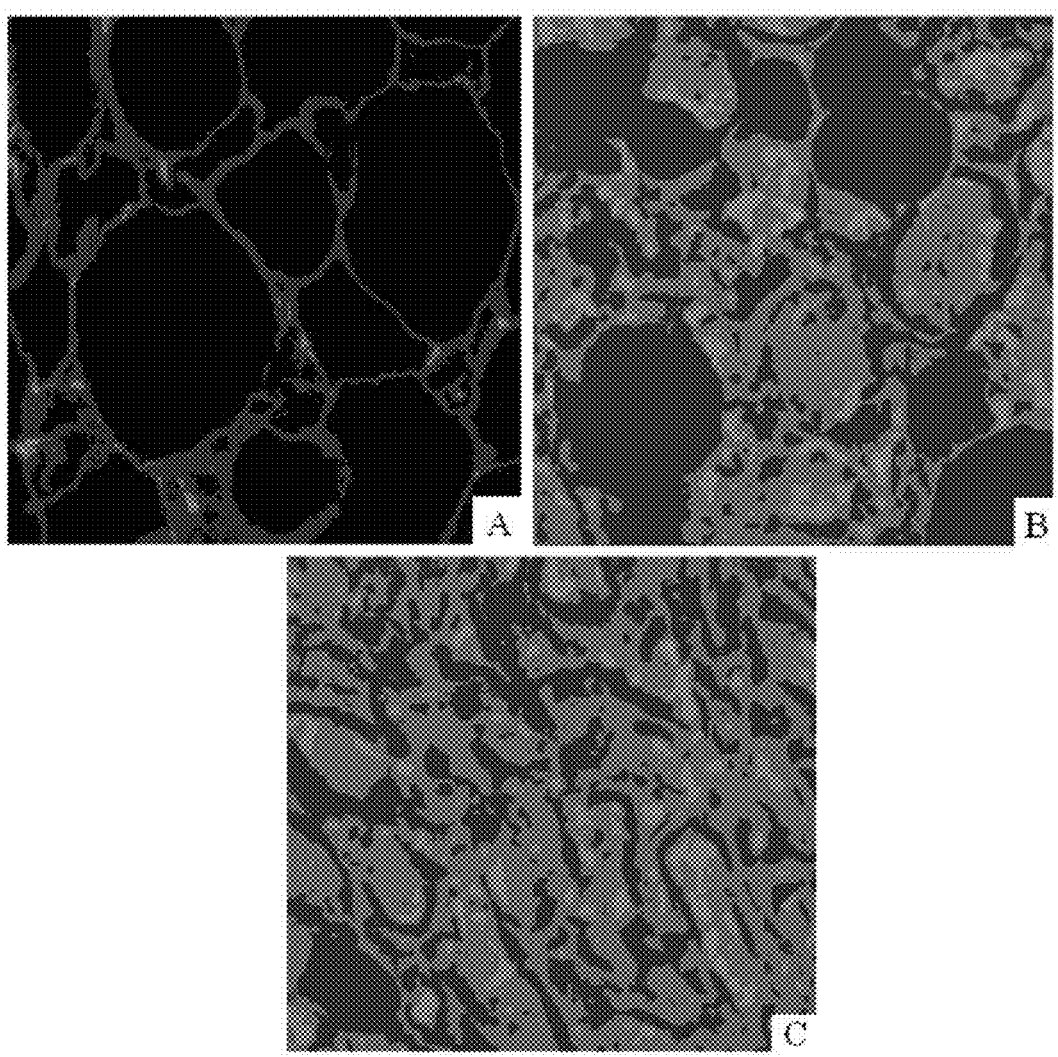
FIG. 5B provides ER binding of Non-invasive Lobular Carcinoma; A. The control; B. The specific binding; C. Non-Specific binding.
Figure 5C:
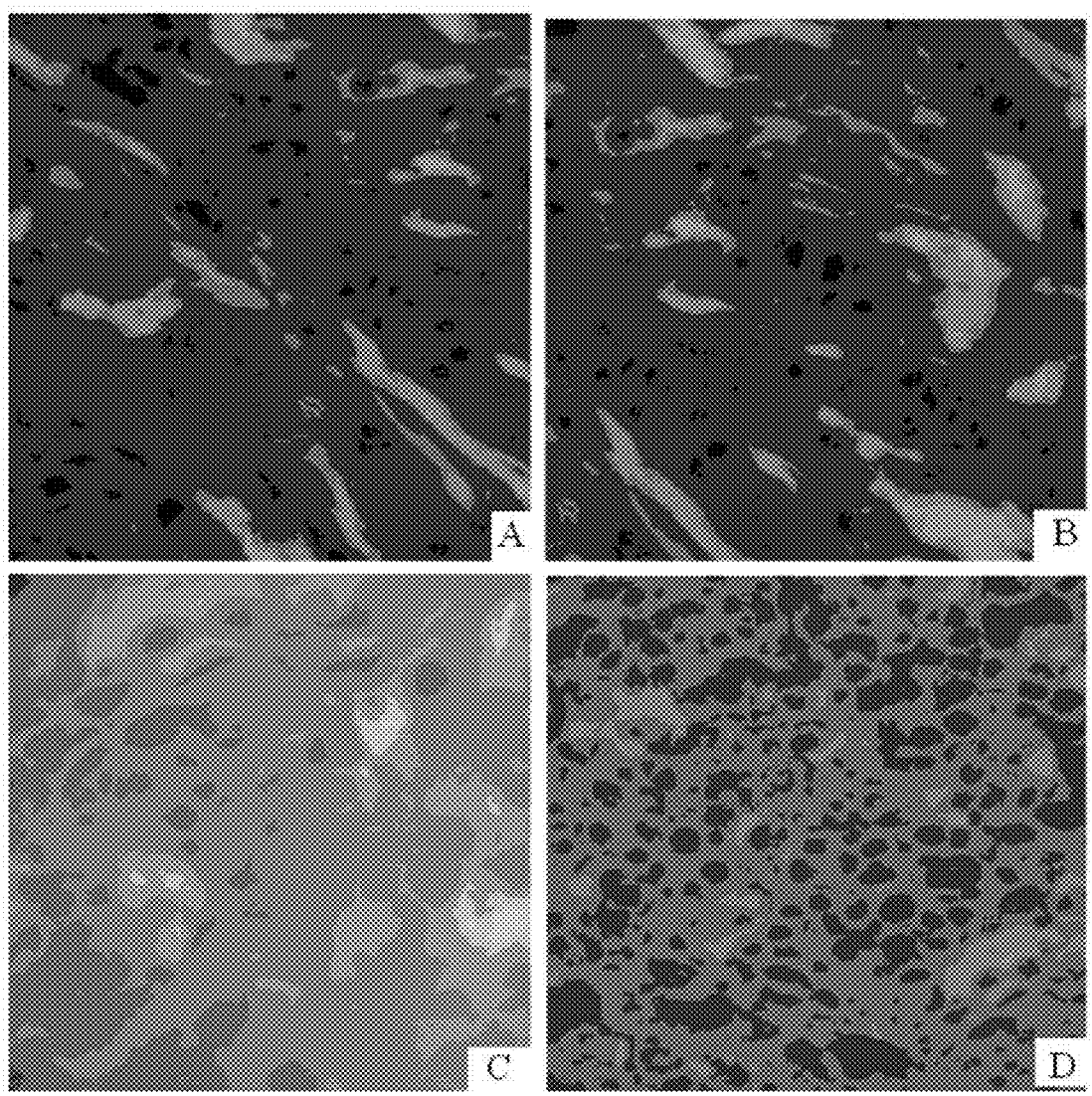
FIG. 5C provides ER binding of Non-invasive Adenocarcinoma and Medullary Carcinoma. (A,B is ER binding of non-invasive Adenocarcinoma; and C,D ER binding of non-invasive Medullary Carcinoma).

The specific ER immunoperoxidase staining is demonstrated exclusively in the nuclei of all the 4 type of carcinoma listed in FIG. 5A (ER binding of Non-invasive Ductal Carcinoma) FIG. 5B (ER binding of Non-invasive Lobular Carcinoma.); FIG. 5C (ER binding of Non-invasive Adenocarcinoma and Medullary Carcinoma). The ER-specific binding covered the nucleus of the positive cell diffusely, but the intensity of the nuclear staining is not always uniform. Frequently, the distribution of positive nuclear staining varied considerably, depending on the area within a section. The heterogeneity of the nuclear staining in distribution and intensity did not correspond to differences in tumor histology. Although no cytoplasmic staining is observed in the frozen sections, it is seen in a few paraffin sections. Moreover, no nuclear staining is observed in the negative controls of paraffin sections. The faint staining seen occasionally in the connective tissue, necrotic tissue, leukocytes and erythrocytes is also regarded as nonspecific, because of its appearance in the negative control sections. Thus, only the nuclear staining is considered specific for ER. Among the positive tissues, the percentage of ER-positive cells ranged from 5% to 72% in paraffin sections. The nuclear staining specific for ER is positive in most of the tumors in the paraffin sections.

J. Specificity of Estradiol Binding to Receptors.

Figure 6:
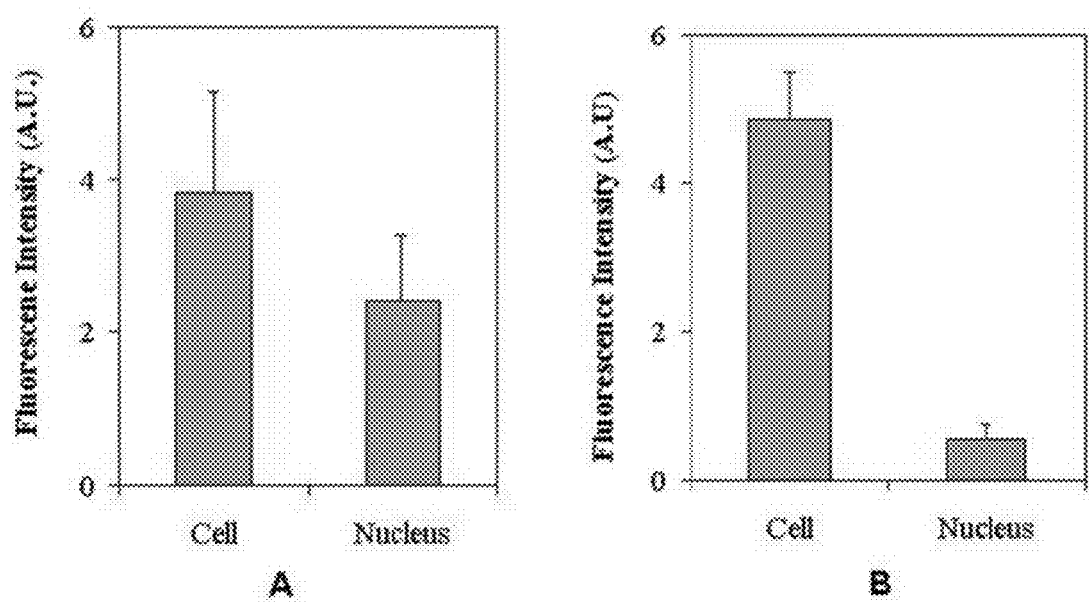
FIG. 6: shows Cellular uptake of Estradiol in the MCF-7 and MDA-MB-231 tumor cell lines.

In-vitro fluorescence signal of malignant cells bearing estrogen receptor positive with the control (cells without intracellular estrogen receptors) are studied. Fluorescence intensity generated by the NIRF Dye-Conjugate in particular to the nucleus and the entire cell is plotted as shown in the (FIG. 6 A, B). The fluorescence intensity of MCF-7 cells are almost higher than the control breast cancer cells. The FIG. 6 shows cellular uptake of Estradiol in the MCF-7 and MDA-MB-231 tumor cell lines. These tumor cells are incubated with NIRFDC (1 μM) up to 60 min and cellular binding and uptake is studied using confocal fluorescent microsope. In particular, FIG. 6A shows the dye-conjugate is internalized and significant amount of binding is seen in the nucleus of MCF-7 cells reflecting receptor positive, whereas in FIG. 6 B: the MDA-MB-231 cells shows a poor binding of conjugate into the nucleus, exhibiting the absence of receptors in the negative control cell line.

K. Method of Preparation of Conjugate Dye

Example 1: Preparation of Conjugate of Estradiol with Bis 1,1-(4-Sulfobutyl) Indotricarbocyanine-5-Carboxylic Acid Sodium Salt Step 1:

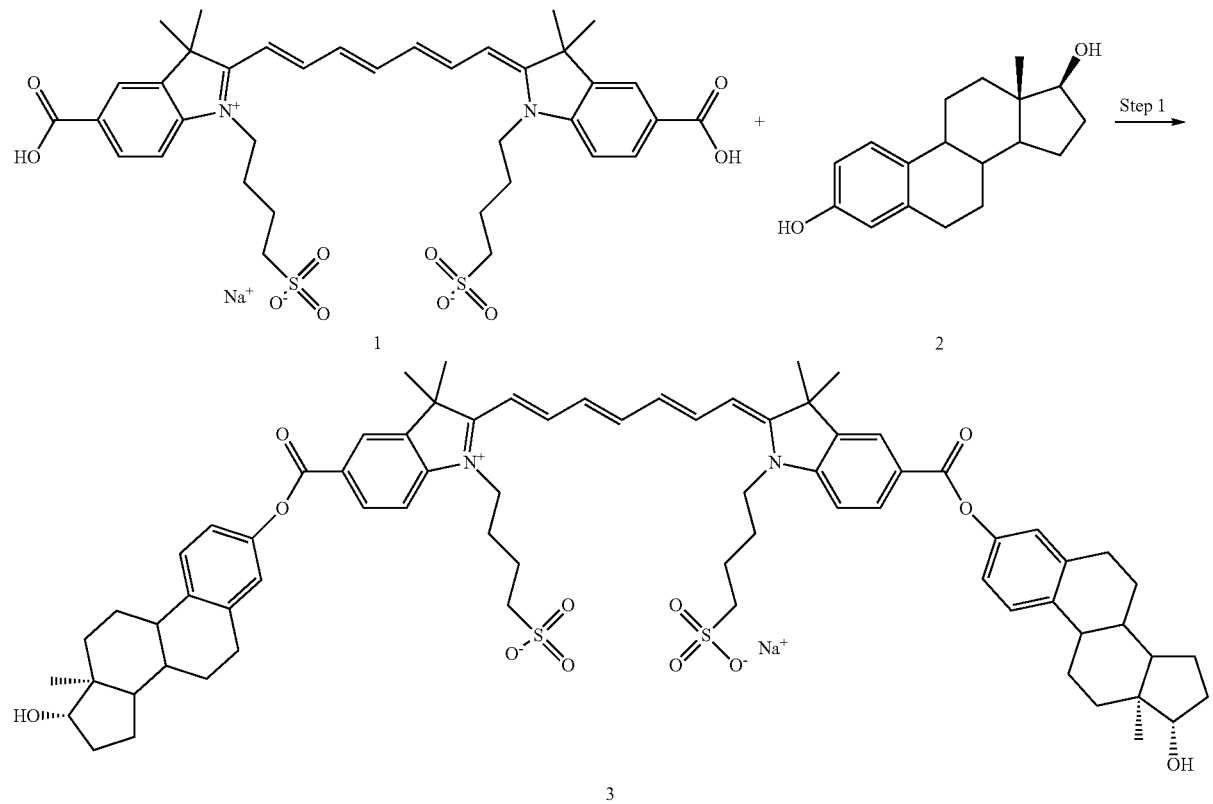

To a solution of compound 1 (400 mg, 0.524 mmol) in dry dimethylformamide (4.0 mL) are added estradiol 2 (357 mg, 1.311 mmol), EDC.HCl (244 mg, 1.573 mmol) and dimethylaminopyridine at about 25° C. The reaction mixture is allowed stir at about 25° C. over a period of 24 h. Upon completion of the reaction the reaction mass is poured into hot ether. The resultant solid is filtered to get crude compound. The crude obtained is further purified by reverse phase column chromatography to get pure compound 3 (126 mg, 10%) as pale green solid.

Step 2:

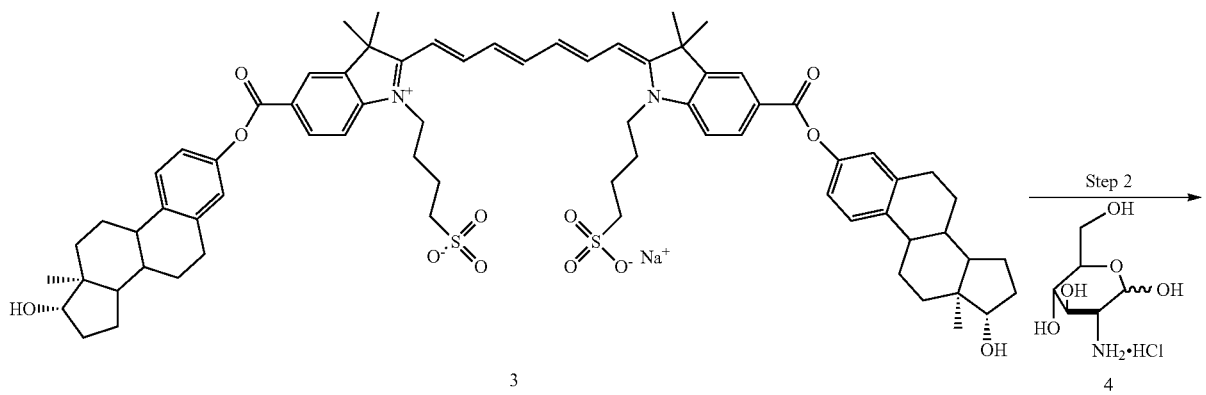

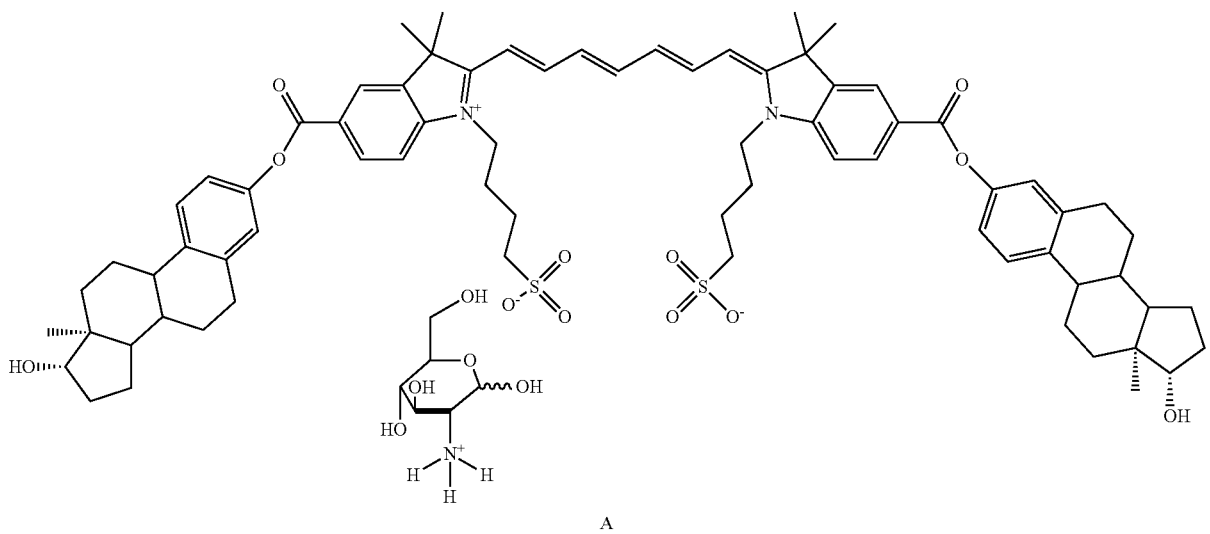

To a solution of compound 3 (55 mg, 0.043 mmol) in dry dimethylformamide (0.7 mL) are added trimethylamine (9.93 mg, 0.098 mmol) and D-glucosamine hydrochloride 4 (10.26 mg, 0.0475 mmol) at about 0° C. The mixture is allowed to stir for 2 h at about 25° C. The resulting reaction mass is poured to methyl tert-butyl ether (MTBE). MTBE solvent is decanted and residue is kept for lyophilization for 3 days to afford 53 mg of final compound as green solid (Formula A).

The present invention thus aims to provide a conjugate for the detection of various cancers, a method of preparation of the said conjugate and method of detecting cancer using said conjugate. The technique offers the potential of non-invasive detection of hormone receptor status in-vivo and help in decreasing the load of unnecessary biopsies. The simplicity involved in the early detection of cancer and economical advantage associated would have a humongous social impact as well.

We claim:
1. A conjugate of formula A:
Formula A
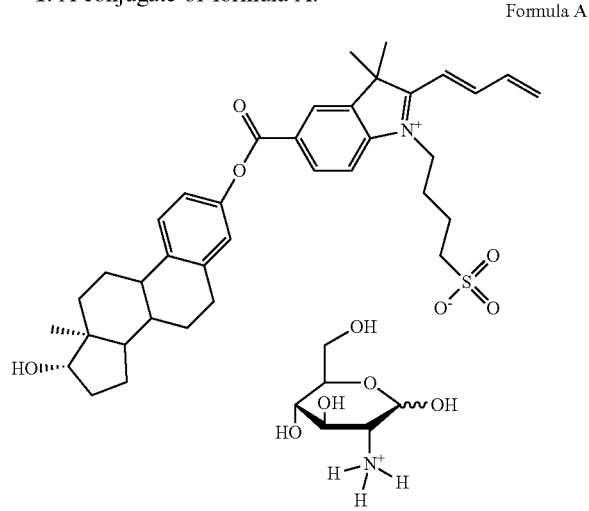
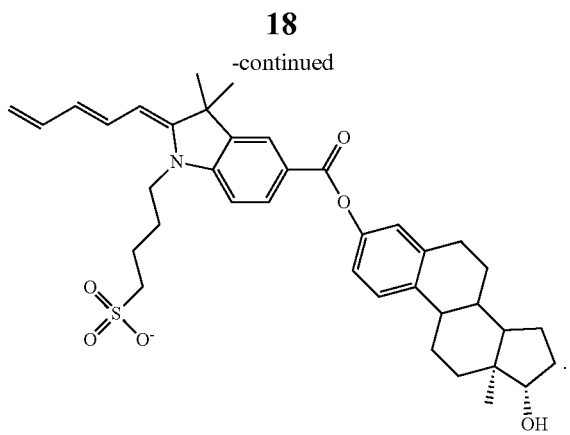
2. A method of preparation of conjugate of formula A,
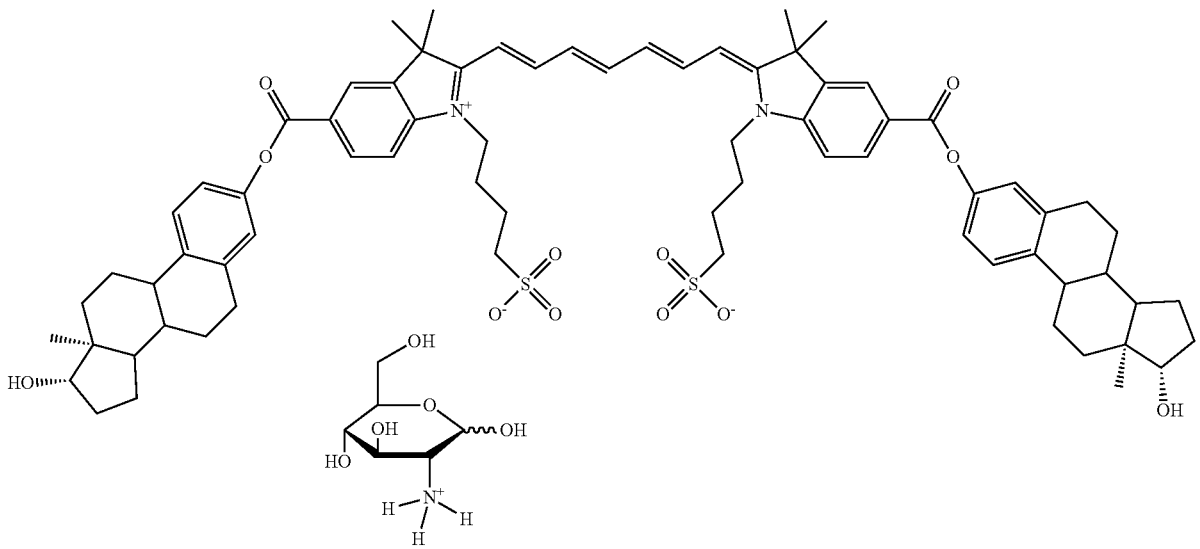
said method comprising:
a) preparing of compound of formula 3; and
Formula 3
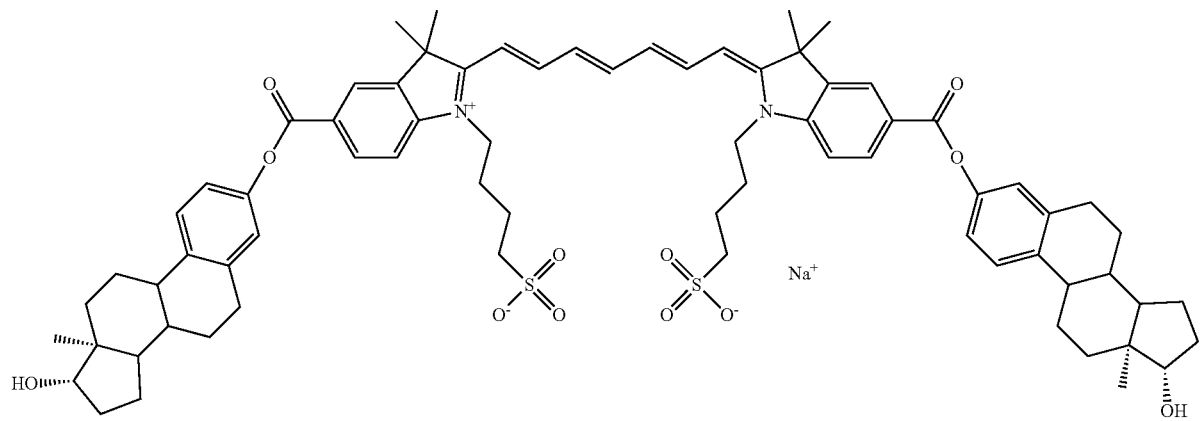

b) treating the compound of formula 3 with D-glucosamine hydrochloride to obtain the conjugate of formula A.

3. The method of preparation of conjugate as claimed in claim 2, wherein the compound of formula 3 is treated with D-glucosamine hydrochloride in presence of trimethylamine.

4. The method of preparation of conjugate as claimed in claim 2, wherein the compound of formula 3 is treated with D-glucosamine hydrochloride at a temperature ranging from 0° C. to 3° C.

5. A method of detection of breast cancer cells, said method comprising:

a) staining breast cells with conjugate of formula A; and

Formula A

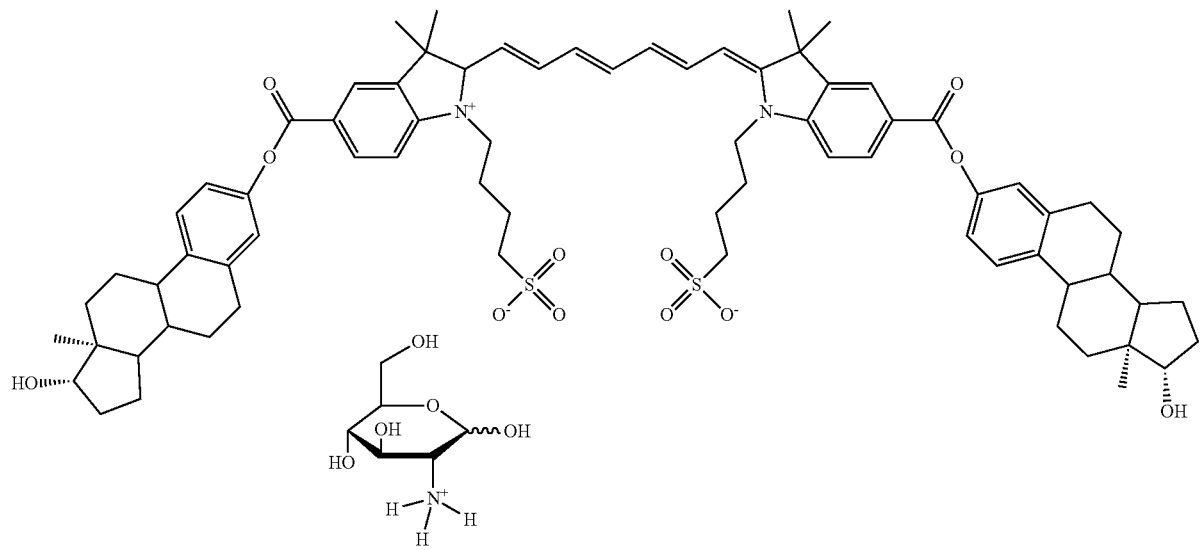

b) comparing the fluorescence intensity generated by the conjugate of formula A at nucleus and the entire cell to detect breast cancer cells.

6. The method as claimed in claim 5, wherein the comparison shows increased fluorescence at the nucleus of the stained breast cancer cells.

* * * * *